United States Patent [19]

Chung, deceased et al.

[11] Patent Number: 4,783,542

[45] Date of Patent: Nov. 8, 1988

[54] SILICONE COMPOUNDS

[75] Inventors: Rack H. Chung, deceased, late of Saratoga County, N.Y.; by Betsy A. Chung, executor, Clifton Park, N.Y.

[73] Assignee: General Electric Company, Waterford, N.Y.

[21] Appl. No.: 497,954

[22] Filed: May 25, 1983

[51] Int. Cl.³ ............................ C07F 7/08; C07F 7/18
[52] U.S. Cl. .................................................. 556/437
[58] Field of Search ........................................ 556/437

[56] References Cited

U.S. PATENT DOCUMENTS

| | | | |
|---|---|---|---|
| 1,918,338 | 7/1933 | Kaufmann | 556/437 |
| 2,836,611 | 5/1958 | Exner et al. | 556/437 |
| 4,139,548 | 2/1979 | Tanaka et al. | 556/437 |
| 4,377,706 | 3/1983 | Hallgren | 556/482 |
| 4,395,526 | 7/1983 | White et al. | 528/18 |

OTHER PUBLICATIONS

"C.A.", 97, 92380, 1982.
Koskinen et al., "Tetrahedron Letters", 24 No. 18, pp. 1951-1952, 1983.
"C.A.", 72, 132859, 1970.
"C.A.", 77, 88572, 1972.
"C.A.", 79, 126564, 1973.
"C.A.", 96, 5895, 1982.

Primary Examiner—Paul F. Shaver

[57] ABSTRACT

Novel enoxy functional silanes of the general formula:

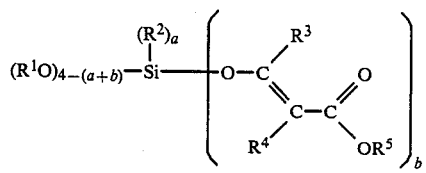

are provided wherein $R^1$ is a monovalent hydrocarbon radical having 1 to 8 carbon atoms; $R^2$, $R^3$ and $R^5$ are monovalent hydrocarbon radicals having 1 to 13 carbon atoms; $R^4$ is hydrogen or a monovalent hydrocarbon radical of 1 to 13 carbon atoms; a is an integer equal to 0 to 3; b is an integer equal to 1 to 4, and the sum of $a+b$ equals 1 to 4.

31 Claims, No Drawings

SILICONE COMPOUNDS

BACKGROUND OF THE INVENTION

The present invention relates to novel silicone compounds. More particularly, the present invention relates to novel enoxy functional silane compounds which are useful as scavenging agents for chemically combined hydroxy groups in one package, moisture curable, room temperature vulcanizable compositions.

Enoxy functional silanes are well known in the art; see for example the patent application of White et al., Ser. No. 277,524, filed June 26, 1981, now U.S. Pat. No. 4,395,526 assigned to the same assignee as the present invention and incorporated herein by reference. White et al. discloses that enoxy functional silanes can be utilized as scavengers for chemically combined hydroxy groups such as methanol to provide room temperature vulcanizable (RTV) compositions which exhibit improved shelf stability. White et al. further discloses that when enoxy functional silanes are used as scavengers there must also be included an effective amount of curing accelerator selected from the group consisting of substituted guanidines, amines and mixtures thereof.

Accordingly, as a part of the research and development of the White et al. composition, the present applicant conducted research into the discovery and development of enoxy functional silanes which did not require the assistance of a curing accelerator. During such research, the novel class of silane compounds of the present invention were discovered. Furthermore, one compound within the novel class of compounds of the present invention was found to be particularly effective as a scavenger composition and hence is specifically disclosed in the White et al. patent application (i.e. methyldimethoxy-2(1-carboethoxy)propenoxysilane).

It is the primary object of the present invention to provide a novel class of enoxy functional silane compositions.

It is a further object of the present invention to disclose a novel class of silanes which are useful as scavenging agents for chemically combined hydroxy groups.

Another object of the present invention is to provide a method for producing the novel enoxy functional silanes of this invention.

Other objects and advantages of the present invention will be obvious from the following detailed description.

SUMMARY OF THE INVENTION

The present invention provides a novel class of enoxy functional silane compounds having the general formula:

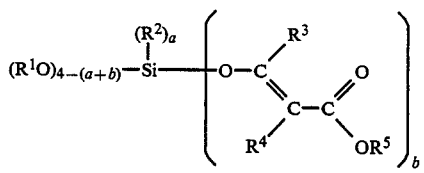

where $R^1$ is a monovalent hydrocarbon radical having 1 to 8 carbon atoms; $R^2$, $R^3$ and $R^5$ are monovalent hydrocarbon radicals having 1 to 13 carbon atoms; $R^4$ is hydrogen or a monovalent hydrocarbon radical having 1 to 13 carbon atoms; a is an integer equal to 0 to 3; b is an integer equal to 1 to 4; and the sum of a+b equals 1 to 4.

DESCRIPTION OF THE INVENTION

In its broadest aspects, the present invention provides novel enoxy functional silanes having the general formula:

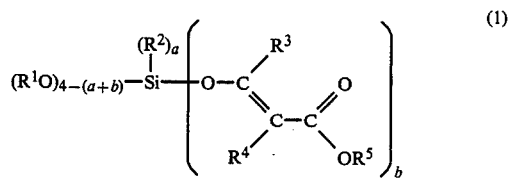

where $R^1$ is a monovalent hydrocarbon radical having 1 to 8 carbon atoms; $R^2$, $R^3$ and $R^5$ are monovalent hydrocarbon radicals having 1 to 13 carbon atoms; $R^4$ is hydrogen or a monovalent hydrocarbon radical having 1 to 13 carbon atoms; a is an integer equal to 0 to 3; b is an integer equal to 1 to 4; and the sum of a+b equals 1 to 4.

Although $R^1$, $R^2$, $R^3$, $R^4$ and $R^5$ can be any suitable monovalent hydrocarbon radical as described hereinabove, preferably they are independently selected from alkyl radicals such as methyl, ethyl and propyl; cycloalkyl radicals such as cyclohexyl and cycloheptyl; alkenyl radicals such as vinyl and allyl; mononuclear aromatic radicals such as phenyl, benzyl and phenylethyl; and fluoroalkyl radicals such as 3,3,3-trifluoropropyl.

One preferred class of compounds coming within the scope of Formula (1) has the formula:

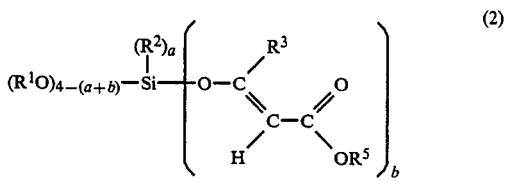

where $R^1$, $R^2$, $R^3$ and $R^5$ a and b are as previously defined. In a preferred embodiment of Formula (2), $R^1$, $R^2$, $R^3$ and $R^5$ are selected from the group consisting of alkyl radicals, cycloalkyl radicals, alkenyl radicals, mononuclear aromatic radicals and fluoroalkyl radicals. Of these radicals, preferably $R^1$, $R^2$, $R^3$ and $R^5$ are all alkyl radicals, and more preferably are selected from the group consisting of methyl, ethyl and propyl radicals. In an even more preferred embodiment $R^3$ is methyl and $R^5$ is ethyl and in the most preferred embodiment $R^1$, $R^2$ and $R^3$ are methyl and $R^5$ is ethyl. Thus one of the most preferred compositions within the scope of Formula (2) is methyldimethoxy-2-(1-carboethoxy)-propenoxysilane. This composition is specifically disclosed as being an effective scavenger compound in the disclosure of White et al. Due to the similarity of structures, all of the compounds of the present invention are believed to be effective scavengers for chemically combined hydroxy groups in RTV compositions of the type described by White et al.

Based upon the disclosure of the Chung/Lucas patent application, Ser. No. 497778 filed concurrently herewith, and which is assigned to the same assignee as the present invention, another particularly preferred embodiment of the present invention has the general formula

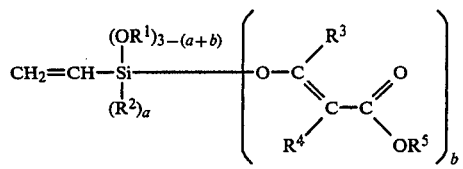

where $R^1$, $R^2$, $R^3$, $R^4$ and $R^5$ are as previously defined, a equals 0 to 2 and b equals 1 to 3.

Chung and Lucas teach that one shortcoming of the White et al. invention is that where $R^1$ and $R^2$ are methyl and X (the hydrolyzable leaving or scavenger group) is enoxy, the elastomeric compositions which form upon curing are translucent but yellow in color. To avoid such yellow coloring it was discovered that silanes having both enoxy and vinyl functionality could be utilized as the scavenger compound. Chung and Lucas teach further that $R^1$ and $R^2$ preferably are lower alkyl groups and most preferably are methyl.

Based upon the teaching of the Chung/Lucas patent application, the preferred radicals for $R^3$, $R^4$ and $R^5$ are the same as disclosed hereinabove. Thus, preferably $R^4$ is hydrogen, methyl, ethyl or propyl and $R^3$ and $R^5$ are methyl, ethyl or propyl. In the most preferred embodiment $R^3$ is methyl, $R^4$ is hydrogen and $R^5$ is ethyl. Accordingly the most preferred compositions within the scope of Formula (3) are vinyldimethoxy-2-(1-carboethoxy)propenoxysilane, methylvinylmethoxy-2-(1-carboethoxy)propenoxysilane and dimethylvinyl-2-(1-carboethoxy)propenoxysilane.

The use of enoxy functional silanes as scavengers for chemically combined hydroxy groups such as methanol or as integrated scavenger-crosslinkers is discussed in greater detail in the patent application of White et al. Accordingly the reader interested in obtaining more in depth information should refer thereto.

Preparation of compositions of the present invention is most easily understood by considering a specific example. Methyldimethoxy-2-(1-carboethoxy)propenoxysilane can be prepared by dissolving 70 g. (0.5M) of methylchlorodimethoxysilane in about 300 g. of dry tetrahydrofuran solvent. To this solution there is added a mixture of 55 g. (0.55M) of triethylamine and 65 g. (0.5M) of ethylacetoacetate over a period of about 45 minutes, maintaining the solution in an ice bath. After stirring at room temperature for 16 hours, triethylaminehydrochlorides are removed by filtration, and the filtrate concentrated on a rotary evaporator to remove low volatiles. The final product is then obtained by distillation at 79° C. and 3 mm Hg (83% yield).

Schematically, the reaction can be viewed as follows:

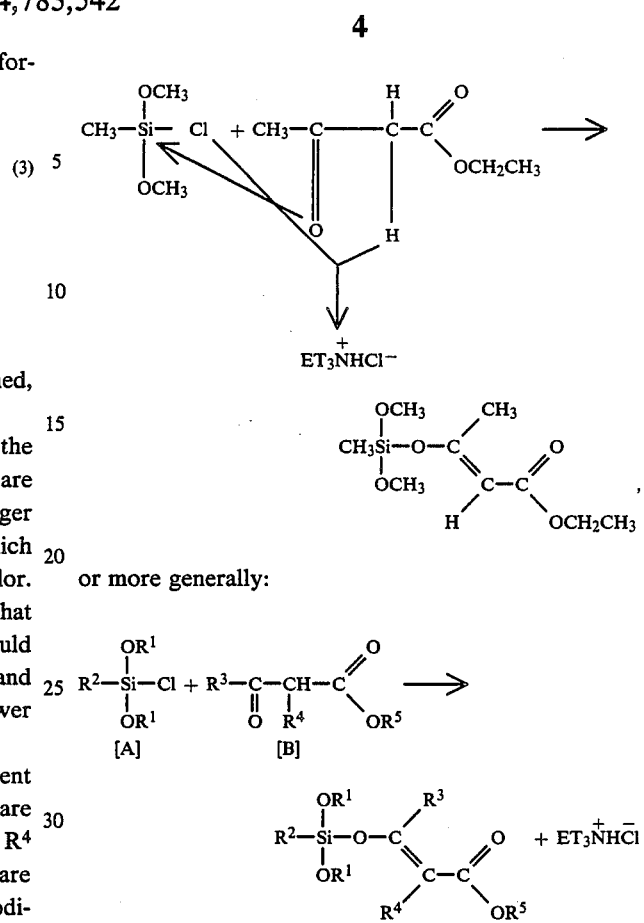

or more generally:

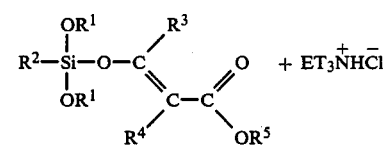

In the foregoing discussion relating to preparing compositions within the scope of the present invention, the skilled artisan without undue experimentation can select from many suitable solvents, however, the present applicant prefers to utilize tetrahydrofuran. Similarly it is not necessary that triethylamine be utilized as its only purpose is to provide a means for removing HCl from the reaction mixture. Although triethylamine is preferred, any compound which accomplishes this purpose can be utilized. Again a variety of such compounds should be evident to the skilled artisan or the suitability of such compounds can be determined without undue experimentation. Of course, the amount of the various ingredients which must be added depends upon the composition being produced. For example, if a compound having two enoxy functional groups is being prepared, twice as much of the ingredient having the formula

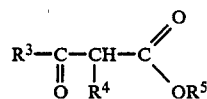

must be utilized if a compound having only one enoxy group is being prepared. That is, the amount of ingredient B which must be added depends upon the number of halogen groups present in ingredient A. Preferably the halogen is chlorine. Again it is assumed that the artisan can determine when the mixture has been reacted for a sufficient period of time. This of course will vary somewhat with the ingredients utilized.

From the foregoing discussion the skilled artisan should be sufficiently instructed so as to be able to provide the silane compositions of the present invention.

The following example is provided to illustrate the utility of the present invention as a scavenger for chemically combined hydroxy groups, thereby providing a one package, moisture curable, room temperature vulcanizable organopolysiloxane composition which has an extended shelf life. However, it should be noted that the following example is given by way of illustration and not by way of limitation.

EXAMPLE

Methyldimethoxy-2-(1-carboethoxy)propenoxysilane was prepared according to the above described method. It was then compounded with hydroxy terminated polymer, filler, butylated guanidine and dibutyltindiacetate under anhydrous conditions using a Semkit ® mixer. A two step catalyzation was employed as follows:

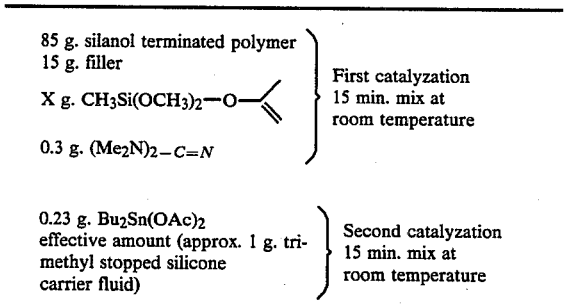

After mixing, the RTV compositions were packaged into sealed aluminum tubes and stored as indicated in Table I. At the end of the aging periods the compositions were cured at room temperature and 50% relative humidity. Speed and degree of cure were determined by tack free time (TFT) and Shore A durometer measurements.

TABLE I

| CH$_3$Si(OCH$_3$)$_2$—O—/CO$_2$Et (grm.) | Shelf Age (days) | TFT R.T. (min.) | TFT 100° | 24 hr/R.T. | Shore/100° |
| --- | --- | --- | --- | --- | --- |
| 2.5 | 1 | 10 | 100 | 28 | 15 |
| 2.5 | 2 | | | | |
| 3.0 | 1 | 10 | 100 | 30 | 23 |
| 3.0 | 2 | | | | |
| 3.5 | 1 | 10 | 90 | | 27 |
| 3.5 | 2 | | | 30 | |
| 4.0 | 1 | 10 | 90 | | 23 |
| 4.0 | 2 | | | 35 | |
| 4.5 | 1 | 10 | 90 | | 29 |
| 4.5 | 2 | | | 29 | |
| 5.0 | 1 | 10 | 90 | | 30 |
| 5.0 | 2 | | | 32 | |

This example illustrates that the novel silicone compositions of the present invention are useful as scavengers for chemically combined hydroxy groups so as to provide RTV compositions having extended shelf life.

I claim:

1. A composition of matter having the general formula:

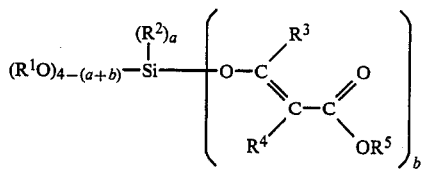

where $R^1$ is a monovalent hydrocarbon radical or fluoroalkyl radical having 1 to 8 carbon atoms; $R^2$, $R^3$, and $R^5$ are monovalent hydrocarbon radicals or fluoroalkyl radicals having 1 to 13 carbon atoms; $R^4$ is hydrogen or a monovalent hydrocarbon radical or fluoroalkyl radical having 1 to 13 carbon atoms; a is an integer equal to 1; b is an integer equal to 1; and the sum of a+b equals 2.

2. The composition of claim 1 wherein $R^1$, $R^2$, $R^3$, $R^4$ and $R^5$ are selected from the group consisting of alkyl radicals, cycloalkyl radicals, alkenyl radicals, mononuclear aromatic radicals and fluoroalkyl radicals.

3. The composition of claim 1 wherein the silane has the general formula:

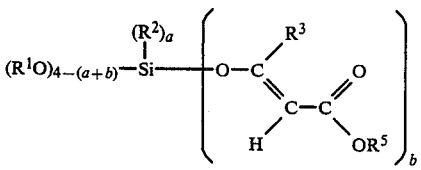

where $R^1$ is a monovalent hydrocarbon radical having 1 to 8 carbon atoms; $R^2$, $R^3$ and $R^5$ are monovalent hydrocarbon radicals having 1 to 13 carbon atoms; a is an integer equal to 0 to 3; b is an integer equal to 1 to 4, and the sum of a+b equals 1 to 4.

4. The composition of claim 3 wherein $R^1$, $R^2$, $R^3$ and $R^5$ are selected from the group consisting of alkyl radicals, cycloalkyl radicals, alkenyl radicals, mononuclear aromatic radicals and fluoroalkyl radicals.

5. The composition of claim 3 wherein $R^1$, $R^2$, $R^3$ and $R^5$ are selected from the group consisting of methyl, ethyl and propyl radicals.

6. The composition of claim 3 wherein $R^3$ is methyl and $R^5$ is ethyl.

7. The composition of claim 5 wherein $R^1$, $R^2$ and $R^3$ are methyl and $R^5$ is ethyl.

8. A composition of matter having the general formula:

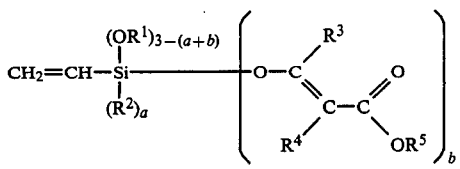

where $R^1$ is a monovalent hydrocarbon radical having 1 to 8 carbon atoms; $R^2$, $R^3$ and $R^5$ are monovalent hydrocarbon radicals having 1 to 13 carbon atoms; $R^4$ is hydrogen or a monovalent hydrocarbon radical having 1 to 13 carbon atoms; a is an integer equal to 0 to 2; b is an integer equal to 1 to 3; and the sum of a+b equals 1 to 3.

9. The composition of claim 8 wherein $R^1$, $R^2$, $R^3$, $R^4$ and $R^5$ are selected from the group consisting of alkyl radicals, cycloalkyl radicals, alkenyl radicals, mononuclear aromatic radicals and fluoroalkyl radicals.

10. The composition of claim 8 wherein the silane has the general formula:

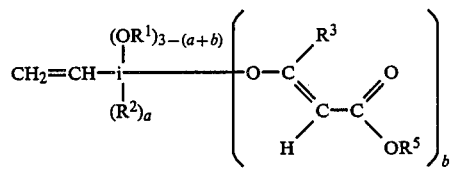

where $R^1$ is a monovalent hydrocarbon radical having 1 to 8 carbon atoms; $R^2$, $R^3$ and $R^5$ are monovalent hydrocarbon radicals having 1 to 13 carbon atoms; a is an integer equal to 0 to 2; b is an integer equal to 1 to 3; and the sum of a+b equals 1 to 3.

11. The composition of claim 10 wherein $R^1$, $R^2$, $R^3$ and $R^5$ are selected from the group consisting of alkyl radicals, cycloalkyl radicals, alkenyl radicals, mononuclear aromatic radicals and fluoroalkyl radicals.

12. The composition of claim 10 wherein $R^1$, $R^2$, $R^3$ and $R^5$ are selected from the group consisting of methyl, ethyl and propyl radicals.

13. The composition of claim 10 wherein $R^3$ is methyl and $R^5$ is ethyl.

14. The composition of claim 12 wherein $R^1$, $R^2$ and $R^3$ are methyl and $R^5$ is ethyl.

15. A method for preparing a composition having the general formula:

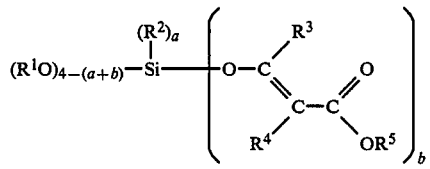

comprising the steps:
(a) dissolving a compound having the formula

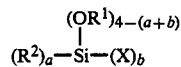

where $R^1$ is a monovalent hydrocarbon radical having 1 to 8 carbon atoms, $R^2$ is a monovalent hydrocarbon radical having 1 to 13 carbon atoms, X is a halogen, a is an integer equal to 0 to 3, b is an integer equal to 1 to 4, and the sum of a+b equals 1 to 4, in a suitable solvent, (b) adding to (a), approximately b equivalents of a compound for removing HX and approximately b equivalents of a compound having the formula:

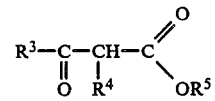

where $R^3$ and $R^5$ are monovalent hydrocarbon radicals having 1 to 13 carbon atoms, $R^4$ is hydrogen or a monovalent hydrocarbon radical having 1 to 13 carbon atoms, (c) stirring the reaction mixture for an effective period of time, and (d) distilling the reacted mixture to obtain the product.

16. The method of claim 1 wherein $R^1$, $R^2$, $R^3$, $R^4$ and $R^5$ are selected from the group consisting of alkyl radicals, cycloalkyl radicals, alkenyl radicals, mononuclear aromatic radicals and fluoroalkyl radicals.

17. A method for preparing a composition having the general formula:

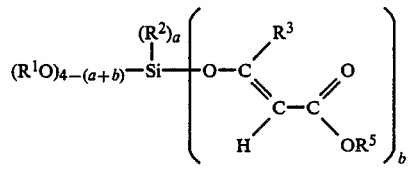

comprising the steps:
(a) dissolving a compound having the formula

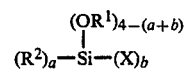

where $R^1$ is a monovalent hydrocarbon radical having 1 to 8 carbon atoms, $R^2$ is a monovalent hydrocarbon radical having 1 to 13 carbon atoms, X is a halogen, a is an integer equal to 1 to 4, and the sum of a+b equals 1 to 4; in a suitable solvent, (b) adding to (a), approximately b equivalents of a compound for removing HX and approximately b equivalents of a compound having the formula:

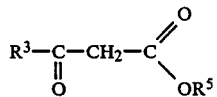

where $R^3$ and $R^5$ are monovalent hydrocarbon radicals having 1 to 11 carbon atoms, (c) stirring the reaction mixture for an effective period of time, and (d) distilling the reacted mixture to obtain the product.

18. The method of claim 17 wherein $R^1$, $R^2$, $R^3$ and $R^5$ are selected from the group consisting of alkyl radicals, cycloalkyl radicals, alkenyl radicals, mononuclear aromatic radicals and fluoroalkyl radicals.

19. The method of claim 17 wherein $R^1$, $R^2$, $R^3$ and $R^5$ are selected from the group consisting of methyl, ethyl and propyl radicals.

20. The method of claim 17 wherein $R^3$ is methyl and $R^5$ is ethyl.

21. The method of claim 19 wherein $R^1$, $R^2$ and $R^3$ are methyl and $R^5$ is ethyl.

22. The method of claim 17 wherein the silane of step (a) has the formula:

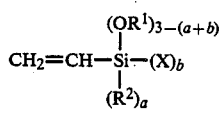

where $R^1$ is a monovalent hydrocarbon radical having 1 to 8 carbon atoms, $R^2$ is a monovalent hydrocarbon having 1 to 13 carbon atoms, X is a halogen, a is an integer equal to 0 to 2, b is an integer equal to 1 to 3, and the sum of a+b equals 1 to 3.

23. The method of claim 22 wherein $R^1$, $R^2$, $R^3$ and $R^5$ are selected from the group consisting of alkyl radicals, cycloalkyl radicals, alkenyl radicals, mononuclear aromatic radicals and fluoroalkyl radicals.

24. The method of claim 15 wherein the solvent is tetrahydrofuran.

25. The method of claim 15 wherein X is chlorine.

26. The method of claim 15 wherein the compound for removing HX is a tertiary amine.

27. The method of claim 26 wherein the tertiary amine is triethylamine.

28. The method of claim 15 wherein after the stirring step HX is removed by filtration of reaction mixture.

29. The method of claim 15 wherein after the stirring step HX is removed by filtration of reaction mixture.

30. The method of claim 29 wherein after filtering, the filtrate is concentrated on a rotary evaporator.

31. The method of claim 15 wherein distillation is effected at approximately 79° C. and approximately 3 mm Hg.

* * * * *

UNITED STATES PATENT AND TRADEMARK OFFICE
CERTIFICATE OF CORRECTION

PATENT NO. : 4,783,542

DATED : November 8, 1988

INVENTOR(S) : Rack H. Chung, deceased, et al.

It is certified that error appears in the above-identified patent and that said Letters Patent is hereby corrected as shown below:

Claim 3, column 6, line 32, between "radical" and "having", please insert -- or fluoroalkyl radical --.

Claim 3, column 6, line 34, between "radicals" and "having", please insert -- or fluoroalkyl radicals --.

Claim 3, column 6, line 35, please delete "0 to 3" and please insert therefor -- 1 --.

Claim 3, column 6, line 35, please delete "to 4".

Claim 3, column 6, line 36, please delete "1 to 4" and please insert therefor -- 2 --.

Claim 8, column 7, line 10, between "radical" and "having", please insert -- or fluoroalkyl radical --.

Claim 8, column 7, line 12, between "radicals" and "having", please insert -- or fluoroalkyl radicals --.

Claim 8, column 7, line 13, between "radical" and "having", please insert -- or fluoroalkyl radical --.

Claim 10, column 7, line 32, between "radical" and "having, please insert -- or fluoroalkyl radical --.

Claim 10, column 7, line 34, between "radicals" and "having", please insert -- or fluoroalkyl radicals --.

Claim 15, column 7, line 66, after "radical", please insert -- or fluoroalkyl radical --.

Claim 15, column 7, line 68, between "radical" and "having", please insert -- or fluoroalkyl radical --.

Claim 15, column 8, line 14, between "radicals" and "having", please insert -- or fluoroalkyl radicals --.

Claim 15, column 8, line 15, between "radical" and "having, please insert -- or fluoroalkyl radical --.

UNITED STATES PATENT AND TRADEMARK OFFICE
CERTIFICATE OF CORRECTION

PATENT NO. : 4,783,542

DATED : November 8, 1988

INVENTOR(S) : Rack H. Chung, deceased, et al.

It is certified that error appears in the above-identified patent and that said Letters Patent is hereby corrected as shown below:

Claim 17, column 8, line 44, after "radical", please insert -- or fluoroalkyl radical --.

Claim 17, column 8, line 46, between "radical" and "having", please insert -- or fluoroalkyl radical --.

Claim 17, column 8, line 47, after "a", please insert -- is an integer equal to 0 to 3, b --.

Claim 17, column 8, line 60, between "radicals" and "having, please insert -- or fluoroalkyl radicals --.

Claim 22, column 9, line 17, between "radical" and "having", please insert -- or fluoroalkyl --.

Claim 22, column 9, line 18, after "hydrocarbon", please insert -- or fluoroalkyl radical --.

Signed and Sealed this

Thirteenth Day of November, 1990

Attest:

HARRY F. MANBECK, JR.

Attesting Officer

Commissioner of Patents and Trademarks